(12) United States Patent
Czysz

(10) Patent No.: US 9,404,086 B2
(45) Date of Patent: Aug. 2, 2016

(54) METHOD FOR CELL DIFFERENTIATION

(71) Applicant: GE HEALTHCARE UK LIMITED, Little Chalfont (GB)

(72) Inventor: Katarzyna Anna Czysz, London (GB)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 125 days.

(21) Appl. No.: 14/225,740

(22) Filed: Mar. 26, 2014

(65) Prior Publication Data
US 2015/0275178 A1 Oct. 1, 2015

(51) Int. Cl.
*C12N 5/071* (2010.01)
*G01N 33/50* (2006.01)

(52) U.S. Cl.
CPC ............. *C12N 5/0672* (2013.01); *C12N 5/067* (2013.01); *G01N 33/502* (2013.01); *G01N 33/5014* (2013.01); *G01N 33/5067* (2013.01); *C12N 2500/62* (2013.01); *C12N 2501/119* (2013.01); *C12N 2501/12* (2013.01); *C12N 2501/155* (2013.01); *C12N 2501/16* (2013.01); *C12N 2501/237* (2013.01); *C12N 2501/33* (2013.01); *C12N 2501/39* (2013.01); *C12N 2506/02* (2013.01); *G01N 2500/04* (2013.01)

(58) Field of Classification Search
CPC ............. C12N 5/0672; C12N 2500/62; C12N 2501/12; C12N 2501/119; C12N 2501/155; C12N 2501/16; C12N 2501/237; C12N 2501/33; C12N 2501/39; C12N 2506/02; G01N 33/5014; G01N 33/5023; G01N 33/5026; G01N 33/56966; G01N 2333/4706; G01N 2500/04
See application file for complete search history.

(56) References Cited

PUBLICATIONS

D'Amour et al., Nature Biotechnology, 23(12): 1534-1541, 2005.*
Chetty et al., Nature Methods, 10: 553-556, published online Apr. 14, 2013, including Supplemental Materials/Methods.*

* cited by examiner

*Primary Examiner* — Thaian N Ton
(74) *Attorney, Agent, or Firm* — Sutherland Asbill & Brennan LLP

(57) ABSTRACT

The present invention relates to the field of cell biology, in particular to methods for differentiating pluripotent stem cells. The invention provides methods for differentiating primate pluripotent stem cells into cells of all three germinal layers. In particular, methods for differentiating primate pluripotent stem cells into the definitive endoderm are provided.

12 Claims, 7 Drawing Sheets
(7 of 7 Drawing Sheet(s) Filed in Color)

METHOD FOR CELL DIFFERENTIATION

FIELD OF INVENTION

The present invention relates to the field of cell biology, in particular to methods for differentiating pluripotent stem cells. The methods of the invention can be used to control and direct the differentiation of pluripotent stem cells into specific germ layers to produce, for example, hepatocyte-like and pancreatic-like cells which find utility in therapy and drug screening.

BACKGROUND TO THE INVENTION

Pluripotent stem cells, such as human embryonic stem cells (hESC) and induced pluripotent stem cells (iPSC), possess the ability to provide an origin for all cell types which are derivatives of the mesoderm, ectoderm and endoderm germinal layers.

In vitro differentiation of pluripotent stem cells to hepatocyte-like cells can potentially generate limitless numbers of cells (Lemaigre, F. P., Gastroenterology, 2009. 137(1), 62-79) with potential for research and therapeutic applications in drug development, detection of drug-induced toxicity, and regenerative medicine. However, the process of differentiation to a specific cell type is often inefficient and lacking in reproducibility. In many instances the competence of cells to acquire an early identity (e.g. definitive endoderm) does not lead to cells being able to successfully commit further to a certain cell type, even when the necessary growth factors and/or small molecules are added in a stage-specific manner (Ochiya, T., Y. Yamamoto, and A. Banas., Differentiation. 2010. 79(2), 65-73).

Definitive endoderm (DE) is formed at approximately 15 days of human embryogenesis and as it gives rise to a variety of organs including liver, its efficient in vitro differentiation is of significant importance. The key finding (D'Amour, K. A., et al., Nat Biotechnol. 2005. 23(12), 1534-41) that exposure of hESC to 100 ng/ml of Activin A in the presence of a low concentration of serum primed a high number of cells to acquire DE identity paved the way for further improvements in differentiation to DE. Activin A was used to mimic Nodal signalling which is crucial during DE development in vivo. While numerous factors have been added to DE specification medium in attempts to improve differentiation (e.g. sodium butyrate, B27 (Hay, D. C., et al., Stem Cells, 2008. 26(4), 894-902; Fletcher, J., et al., Cloning Stem Cells, 2008. 10(3), 331-9); Albumin fraction V, (Cai, J., et al., Hepatology, 2007. 45(5), 1229-39); FGF4 and BMP2 (Hannan, N. R., et al., Nat Protoc, 2013. 8(2), 430-7); Wnt3a and HGF (Chen, Y. F., et al., Stem Cells Dev, 2010. 19(7), 961-78), the use of 100 ng/ml of Activin A as a principal differentiation agent is well established.

Despite these investigations the expression of the pluripotency transcription factors OCT4 and NANOG remain difficult to down regulate effectively (Hay, D. C., et al., Stem Cells, 2008. 26(4): 894-902; Synnergren, J., et al., Stem Cells Dev, 2010. 19(7), 961-78; Touboul, T., et al., Hepatology, 2010. 51(5), 1754-65) suggesting that hESC responses to differentiating factors may be hindered to some extent. There therefore remains a need for simple, cost effective and efficient methods of directing the differentiation process of hESC, iPSC and other primate pluripotent stem cells (pPSC) into cells of the endoderm, mesoderm or ectoderm lineage. In particular, there is a need for a simple and robust method to optimise the differentiation of pluripotent human stem cells to definitive endoderm.

The present invention addresses these problems and provides methods for producing cells of the endoderm, mesoderm and endoderm lineage which have utility in in vitro screening (e.g. for drug development and toxicology studies) and therapy.

SUMMARY OF THE INVENTION

The present invention provides methods which can be used to direct differentiation of pPSC into cells of the endoderm, mesoderm or ectoderm lineage. Particular embodiments of the invention provide methods for directing differentiation of primate pluripotent stem cells into definitive endoderm.

According to a first aspect of the present invention, there is provided a method for producing definitive endoderm (DE) cells from pPSC comprising culturing pPSC in a medium comprising Activin A and dimethyl sulfoxide (DMSO), thereby producing DE cells that express a gene selected from the group consisting of SOX17, CXCR4 and GATA4.

The advantage of the method is that it produces high yields of DE cells that can be differentiated further into other cell types of the endoderm lineage, such as hepatocytes or pancreatic cells.

In one embodiment, Activin A is present in a medium at a concentration in a range from 50 ng/ml to 150 ng/ml.

In another embodiment, Activin A is present in a medium at a concentration of 100 ng/ml.

In a further embodiment, the pPSC are cultured in the presence of varying concentrations of DMSO.

In one embodiment, the DMSO is present in a medium at a concentration in a range from 0.25% to 2% volume/volume (v/v). Preferably, the DMSO is present in the medium at a concentration in the range from 0.25% to 0.75% v/v. More preferably, the DMSO is present in the medium at a concentration in the range from 0.5% to 0.6% v/v.

In another embodiment, the pPSC are initially cultured in the presence of a high concentration of DMSO and then cultured in the presence of a low concentration of DMSO.

In a further embodiment, the medium additionally comprises one or more growth factors or modulators selected from the group consisting of FGF2, Wnt3a, SFRP5 and LY294002.

In one embodiment, the pPSC are cultured in the medium for 3 to 5 days. Preferably, the pPSC are cultured in the medium for 4 days.

In another embodiment, the pPSC are selected from the group consisting of human embryonic stem cells, induced pluripotent stem cells and mesenchymal stem cells.

In a further embodiment, the method of the first aspect of the invention further comprises differentiating the DE cells in a medium comprising DMSO, thereby producing hepatic-like cells or pancreatic-like cells.

In one embodiment, the method of the first aspect of the invention comprises culturing said DE cells in a medium comprising a DMSO and a growth factor or modulator selected from the group consisting of BMP2, FGF4 and BMP4, thereby producing hepatic-like cells that express ALB.

In accordance with a second aspect of the present invention, there is provided a hepatic-like cell produced by the method as hereinbefore described.

According to a third aspect of the present invention, there is provided a pancreatic-like cell produced by the method as hereinbefore described.

In accordance with a fourth aspect of the present invention, there is provided a method for screening a test compound for its effect on a hepatocyte, comprising contacting a hepatic-like cell as described herein with a test compound and determining any change in the morphology, phenotype, physiology, gene expression or viability of the hepatic-like cell in the absence of the test compound.

According to a fifth aspect of the present invention, there is provided a method for screening a test compound for its effect on a pancreatic-like cell, comprising contacting a pancreatic-like cell as herein described with a test compound and determining any change in the morphology, phenotype, physiology, gene expression or viability of the pancreatic-like cell in the absence of the test compound.

In accordance with a sixth aspect of the present invention, there is provided a method for producing mesoderm cells from pPSC comprising culturing the pPSC in a medium comprising Activin A and DMSO, thereby producing mesoderm cells that express a gene selected from the group consisting of NCAM/CD56, KDR, PDGRF-α, CD10, CD34, CD73, CD105, CD146 and CD166. In a preferred embodiment, the mesoderm cells are cardiomyocytes.

According to a seventh aspect of the present invention, there is provided a method for producing ectoderm cells from pPSC comprising culturing the pPSC in a medium comprising Activin A and DMSO, thereby producing ectoderm cells that express a gene selected from the group consisting of MAP2, PAX6 and NEUROD1. In a preferred embodiment, the ectoderm cells are neurons.

In accordance with an eighth aspect of the present invention, there is provided a use of a hepatic-like cell as hereinbefore described in drug or toxicity screening According to a ninth aspect of the present invention, there is provided a use of a pancreatic-like cell as hereinbefore described in drug or toxicity screening.

In accordance with a tenth aspect of the present invention, there is provided a use of a hepatic-like cell or a pancreatic-like cell as hereinbefore described in therapy.

BRIEF DESCRIPTION OF THE FIGURES

The file of this patent contains at least one drawing/photograph executed in color. Copies of this patent with color drawing(s)/photograph(s) will be provided by the Office upon request and payment of the necessary fee.

DETAILED DESCRIPTION OF THE INVENTION

Definitions

Figure 1:
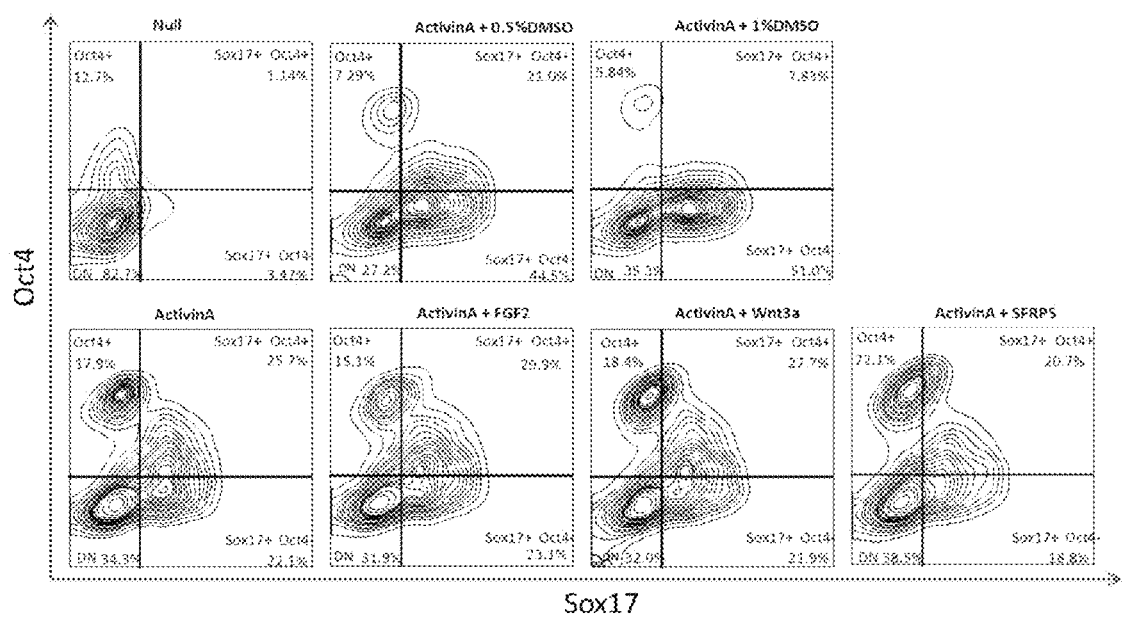
FIG. 1 shows flow cytometry analysis of differentiation markers at day 4 of DE differentiation.

As used herein, the term 'primate pluripotent stem cell' (pPSC) refers to cells of primate origin which have the characteristic of being capable under appropriate conditions of producing progeny of different cell types that are derivatives of all of the three germinal layers (i.e., endoderm, mesoderm and ectoderm) or the ability to form identifiable cells of all three germ layers in tissue culture. Included in the definition of pluripotent stem cells are embryonic cells of various types, exemplified by human embryonic stem cells (hESC), described by Thomson et al. (Science, 1998. 282, 1145-47), induced pluripotent stem cells (iPSC), described by Takahashi et al. (Cell, 2007. 131, 861-872) produced by reprogramming differentiated cells and parthenogenetic human embryonic stem cells (phESC), described by Revazova et al. (Cloning Stem Cells. 2007, 9 (3), 432-449), derived from an embryo produced without fertilisation.

Recently Kilmanskaya et al. (Nature, 2006. 444, 481-485) described a single blastomere biopsy method for isolating hESC from single blastomeres without destroying the embryo. Furthermore Chung et al. (Cell Stem Cell, February 2008. 2(2), p. 113-7) demonstrated the derivation of five hESC lines without embryo destruction, including one without hESC co-culture. The blastomeres were removed using a technique similar to pre-implantation genetic diagnosis and the procedure did not appear to interfere with subsequent blastocyst development of the parent embryo.

For the avoidance of doubt, any cells of primate origin which are fully pluripotent (capable of producing progeny that are derivatives of all three germinal layers) are included in the definition of pPSC, regardless of whether or not they are derived from embryonic tissue, foetal tissue, adult tissue (e.g. iPSC) or other sources.

Culture of Undifferentiated hESC

The H1 human ES cell line was acquired from WiCell Research Institute (Madison, Wis.), propagated on Matrigel-coated vessels (around 0.3 mg/ml when coating) and cultured in mTeSR (both obtained from StemCell Tech). The H7 human ES cell line was propagated and maintained on Matrigel coated vessels in X-Vivo10 Medium (Lonza), supplemented with 80 ng/ml FGF2 and 0.5 ng/ml TGFBI (R&D Systems) in feeder-free, serum-free conditions. Cells were passaged when approximately 80% confluent by treatment with 5 mg/ml Collagenase IV for 5 min, washing with PBS and trypsynized with 0.25% Trypsin-EDTA (all from Life Technologies). 10% FBS (PAA) in RPMI 1640 medium (Life Technologies) was used to stop trypsinization. The number of total and viable cells was determined using a NucleoCounter YC-100 (Chemometec). Collagenase IV was used to detach the boundaries of colonies in the flasks to be passaged. The cells were then washed with PBS, scraped in medium and passaged onto new Matrigel coated vessels at the cell density of $0.5$-$0.6 \times 10^5$ cells/cm$^2$. Medium was changed daily.

Differentiation of hESC

Definitive endoderm formation: hESC were passaged onto the appropriate culture flasks or plates at $0.6 \times 10^5$ cells/cm$^2$ and cultured for 2 days. To initiate definitive endoderm differentiation hESC were washed once with PBS and cultured in RMPI 1640 medium (Life Technologies) supplemented with 100 ng/ml of Activin A (R&D Systems) and 0.25 to 2% of DMSO (Sigma). FBS (0.2%) was added after first 24 hours and cells were cultured for four days with media changed daily.

Hepatic specification: hESC-derived definitive endoderm cells were washed once with PBS and cultured in KO-DMEM medium and 2% KOSR supplemented with 1 mM L-glutamine, NEAA (all from Life Technologies), B-Mercaptoethanol (Sigma), 30 ng/ml BMP2, 10 ng/ml FGF4, 0.5% DMSO for 5 days with BMP4. Hepatoblast-like cells were then washed with PBS, trypsynised and plated onto new Matrigel-coated vessels at $0.4 \times 10^5$ cells/cm$^2$ and cultured in the same medium for subsequent 3 days but with BMP4 substituted for 10 ng/ml HGF. Next, cells were washed with PBS and cultured for six days in HepatoZYME medium (Life Technologies) supplemented with 2% FBS, 1 mM L-glutamine, 2 ug/ml Insulin (Roche), 2 ug/ml Ascorbic Acid (Sigma), $10^{-7}$M Dexamethasone (Sigma), 10 ng/ml HGF and 10 ng/ml OSM (R&D Systems) with daily medium changes. Cells were then for cultured for ten days in L-15 medium (Phenol Red-free, Life Technologies) supplemented with 2% FBS, 2 ug/ml Ascorbic Acid, 10 mM HEPES (Life Technologies), 2 ug/ml Insulin, $10^{-7}$M Dexamethasone, and 10 ng/ml OSM with daily medium changes.

HepG2 Culture

The liver hepatocellular carcinoma HepG2 cell line (ATTC) was cultured in RPMI 1640 medium supplemented with 1 mM L-Glutamine, NEAA 10% FBS on poly-D-lysine coated vessels at the density of $0.4 \times 10^5$ cells/cm$^2$ for two days before use.

Immunofluorescence Analysis

For detection of stage-specific markers, cells were grown and differentiated in 96 well plates (uClear black plate with clear flat bottom, Greiner). Cells were rinsed twice with PBS and fixed in 4% paraformaldehyde (USB) for 15 min at room temperature and then washed twice with PBS and blocked for 30 min at RT in 1% BSA (Life Technologies) and 0.1 mg/ml human IgG (Sigma) in perm/wash buffer (BD). Cells were subsequently stained for 2 hours at RT or overnight at 4° C. with primary rabbit anti-OCT4 (Cell Signaling), mouse and anti-SOX17 (Abcam) antibodies diluted in perm/wash buffer. Cells were subsequently washed several times with perm/wash buffer and incubated at 4° C. in the dark with goat anti-mouse-FITC and chicken anti-rabbit-Cy5 (Molecular probes) diluted 1:400 in perm/wash buffer. After 1 hour incubation, cells were washed several times with PBS and incubated with Hoechst 33342 (Life Technologies) for 15 min at room temperature. After subsequent washing with PBS, 96 well plates were then imaged on IN Cell Analyzer 2000 (GE Healthcare).

Flow Cytometry Analysis

Cells cultured in 6 well plates were washed twice in PBS and treated with 0.25% trypsin-EDTA (Life Technologies) to obtain single cell suspensions. Trypsin was inactivated after 5 min of incubation by adding medium containing 10% FBS. Cells were counted, centrifuged at 300 g for 5 min, washed twice with PBS and subsequently fixed in 2% paraformaldehyde (USB). Following 15 min incubation at room temperature cells were washed in PBS and perm/wash buffer (PWB) (BD) and subsequently resuspended at $4 \times 10^6$ cells/ml in perm/wash buffer supplemented with 0.1 mg/ml human IgG (Sigma) and 10% serum from the species of secondary antibody (Life Technologies). Cells were incubated for 30 min at 4° C. and then 50 µl aliquots ($2 \times 10^5$ cells) were transferred to individual 5 ml polystyrene round-bottom FACS assay tubes. For double staining of cells with OCT4 and SOX17, cells were stained in perm/wash buffer first with mouse anti-OCT4 (Cell Signalling) and incubated for 1 h at room temperature, following by two washes with PBS and incubation in perm/wash buffer with goat anti-mouse-FITC (Molecular Probes) and goat anti-SOX17-APC (R&D Systems). Following 1 h incubation at 4° C., samples were washed twice and resuspended in 0.2% FBS in PBS in a final volume of 3000/tube. Separate staining for OCT4 and SOX17 was performed analogously. Cells were analysed on a BD FACSCalibur flow cytometer and data analysed using CellQuest software.

qRT-PCR Analysis

Isolation of total cellular RNA was performed using an illustra RNAspin Mini RNA Isolation Kit (GE Healthcare) and the concentration of RNA in each sample measured on a NanoDrop 1000 spectrophotometer. 1 µg of extracted total RNA was reverse transcribed using High Capacity cDNA Reverse Transcription Kit (Applied Biosystems). TaqMan quantitative PCR was performed using unlabelled PCR primers and FAM-based probes (Applied Biosystems by Life Technologies) in conjunction with TaqMan Universal PCR Master Mix, No AmpErase UNG (Applied Biosystems). Concentrated TaqMan PCR Master Mix (2x) was combined with water and cDNA. The final concentration of Master Mix was achieved by addition of appropriate concentrations of primers/FAM probes diluted in water. Reactions were carried out on a 7900HT Fast Real-Time PCR System (Applied Biosystems). qRT-PCR cycling conditions were: 95° C. for 10 min, and subsequently 45 cycles of 95° C. for 10 sec and 60° C. for 1 min. Each sample was run in triplicate with GAPDH as a reference gene. Analysis of results was performed in SDS Software for the 7900HT Fast Real-Time PCR System. Relative quantification was calculated against GAPDH and B-Actin housekeeping genes and standard derivations report n=3 replicates from each sample.

Results

Figure 2:
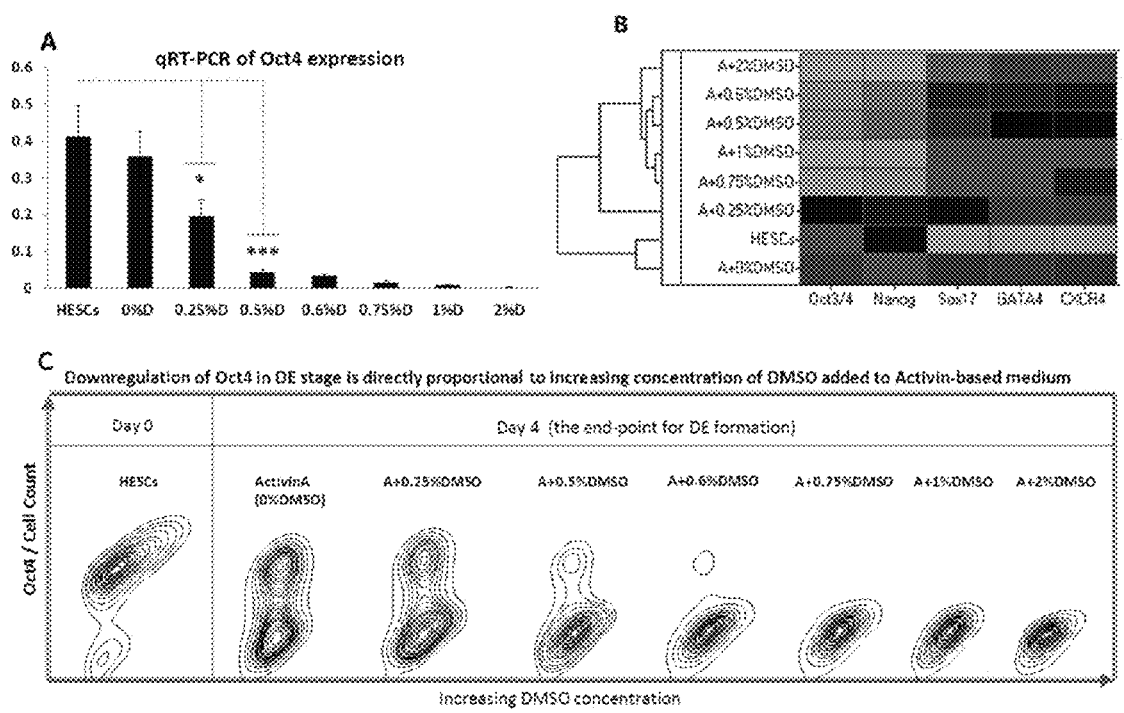
FIG. 2 shows qRT-PCR (A&B) and flow cytometry (C) analysis of differentiation markers at day 4 of DE differentiation

Analysis of OCT 4 and SOX 17 expression by flow cytometry (FIG. 1) showed that addition of 0.5% and 1% DMSO to Activin A containing medium produced a decrease in OCT4 expressing cells and an increase in SOX17 expressing cells relative to control cells treated with Activin A alone. Nodal signalling is crucial for the specification of definitive endoderm in vertebrates in vivo and use of Activin A at 100 ng/ml is standard practice in the field to recapitulate this signalling pathway in vitro to stimulate differentiation to DE. The growth factors FGF2 and Wnt3a have been reported to aid in DE differentiation (D'Amour, K. A., et al., Nat Biotechnol, 2005. 23(12), 1534-41; D'Amour, K. A., et al. Nat Biotechnol, 2006. 24(11), 1392-401) when used in conjunction with Activin A. Supplementation of Activin A with either FGF2 or Wnt3a proved to yield inferior differentiation to DE when compared with Activin A and DMSO (FIG. 1).

qRT-PCR and further flow cytometry analysis (FIG. 2) confirmed the action of DMSO in promoting DE formation when used to potentiate the action of Activin A. qRT-PCR (FIGS. 2A & B) showed that increasing concentrations of DMSO produced a significant dose dependent decrease in OCT4 expression and up regulation of SOX17, GATA4 and CXCR4, with down regulation of OCT4 confirmed by flow cytometry analysis (C).

Figure 3:
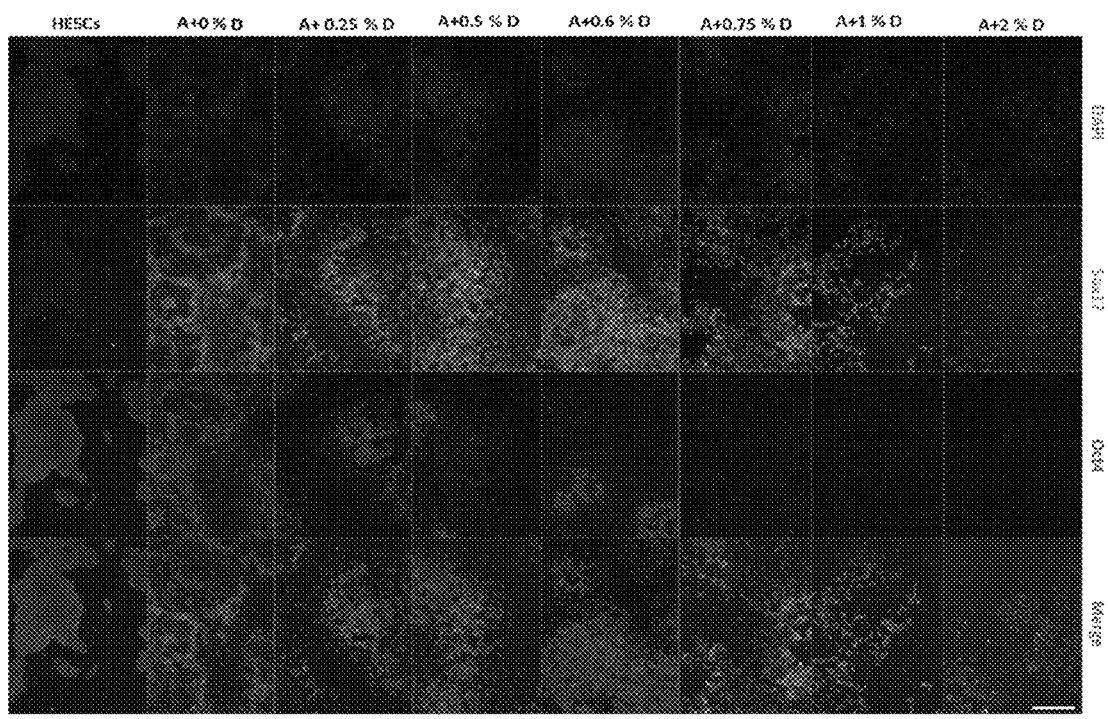
FIG. 3 shows immunofluorescence analysis of differentiation markers at day 4 of DE differentiation.

Further analysis of DMSO enhancement of Activin A driven differentiation to DE by immunofluorescence imaging (FIG. 3) confirmed that increasing concentrations of DMSO (A+X % DMSO) produced down regulation of OCT4 expression from 0% to 2% DMSO. SOX 17 staining was maximum at 0.6% DMSO. These data indicate an optimum concentration range for DMSO of 0.5% to 0.6%.

Figure 4:
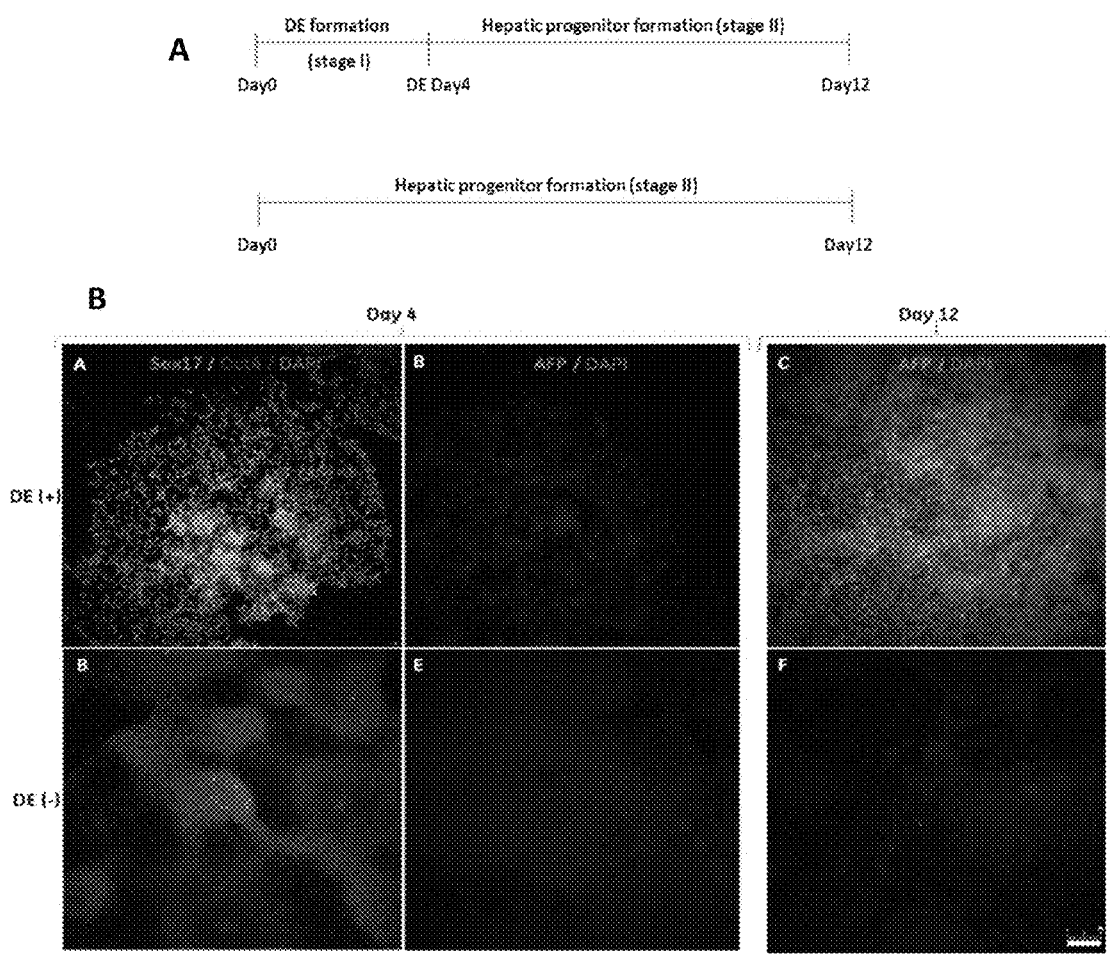
FIG. 4 shows immunofluorescence analysis of differentiation markers at day 4 and 12 of DE and hepatic progenitor differentiation. (A) Schematic of stage 1 and stage 2 differentiation procedures. (B) Immunofluorescence staining of differentiation markers.

Treatment of cells with Activin A+DMSO in a preliminary DE specification stage 1 was found to be essential for further differentiation of cells towards a hepatic phenotype (FIG. 4). Treatment of cells with Activin A and DMSO produced significant down regulation of OCT4 and up regulation of Sox17 at day 4 (FIG. 4B; A) which was not observed in the absence of this initial specification step (FIG. 4B; B), inclusion of the initial Activin A+DMSO stage 1 specification step also up regulated cell AFP expression (FIG. 4B; C) at day 12 of differentiation towards hepatic like cells compared to cells not primed with Activin A and DMSO (FIG. 4B; F).

Figure 5:
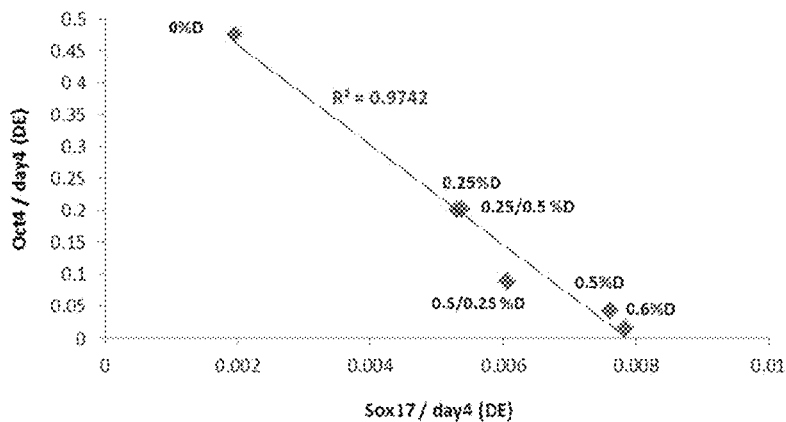
FIG. 5 shows correlation analysis of qRT-PCR data for differentiation markers.
Figure 5:
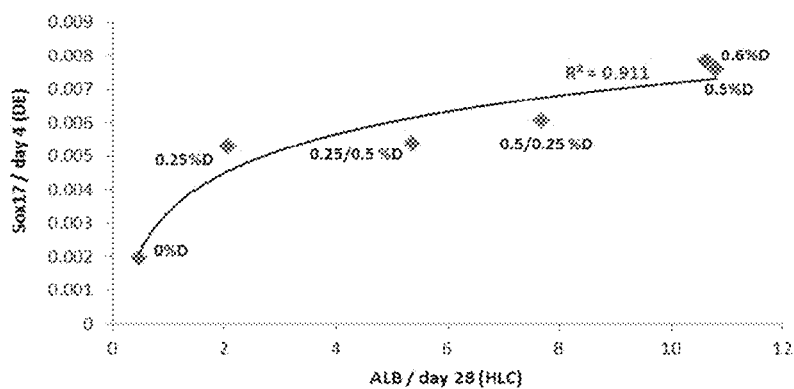
Figure 5:
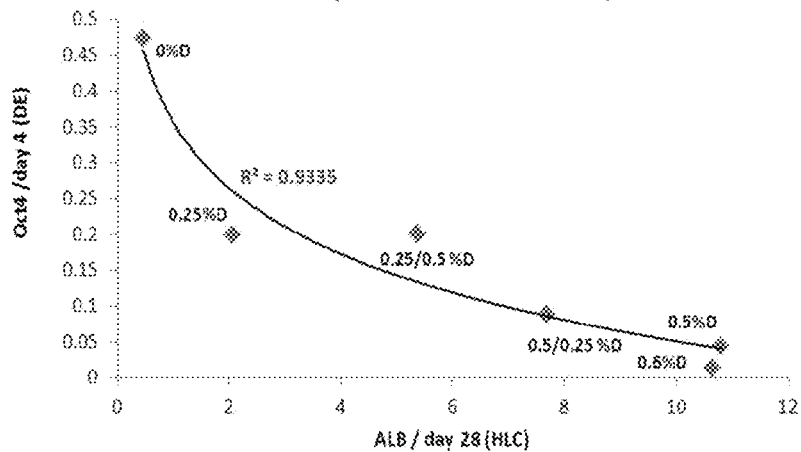

Correlation analysis of marker gene expression (FIG. 5) confirmed the enhancement of differentiation provided by DMSO across the full extent of differentiation from DE to hepatic like cells. Linear correlation of OCT4 down regulation and SOX17 up regulation at day 4 of DE differentiation was observed (FIG. 5A) in the presence of different concentrations of DMSO (X % DMSO). Good correlation (FIG. 5B) was also observed between increasing SOX17 at day 4 (definitive endoderm) and ALB expression at day 28 (hepatic like cells) with increasing concentrations of DMSO (X % DMSO). Finally good correlation was recorded (FIG. 5C) between decreased OCT4 at day 4 (definitive endoderm) and increased ALB expression at day 28 (hepatic like cells) with increasing concentrations of DMSO (X % DMSO).

Figure 6:
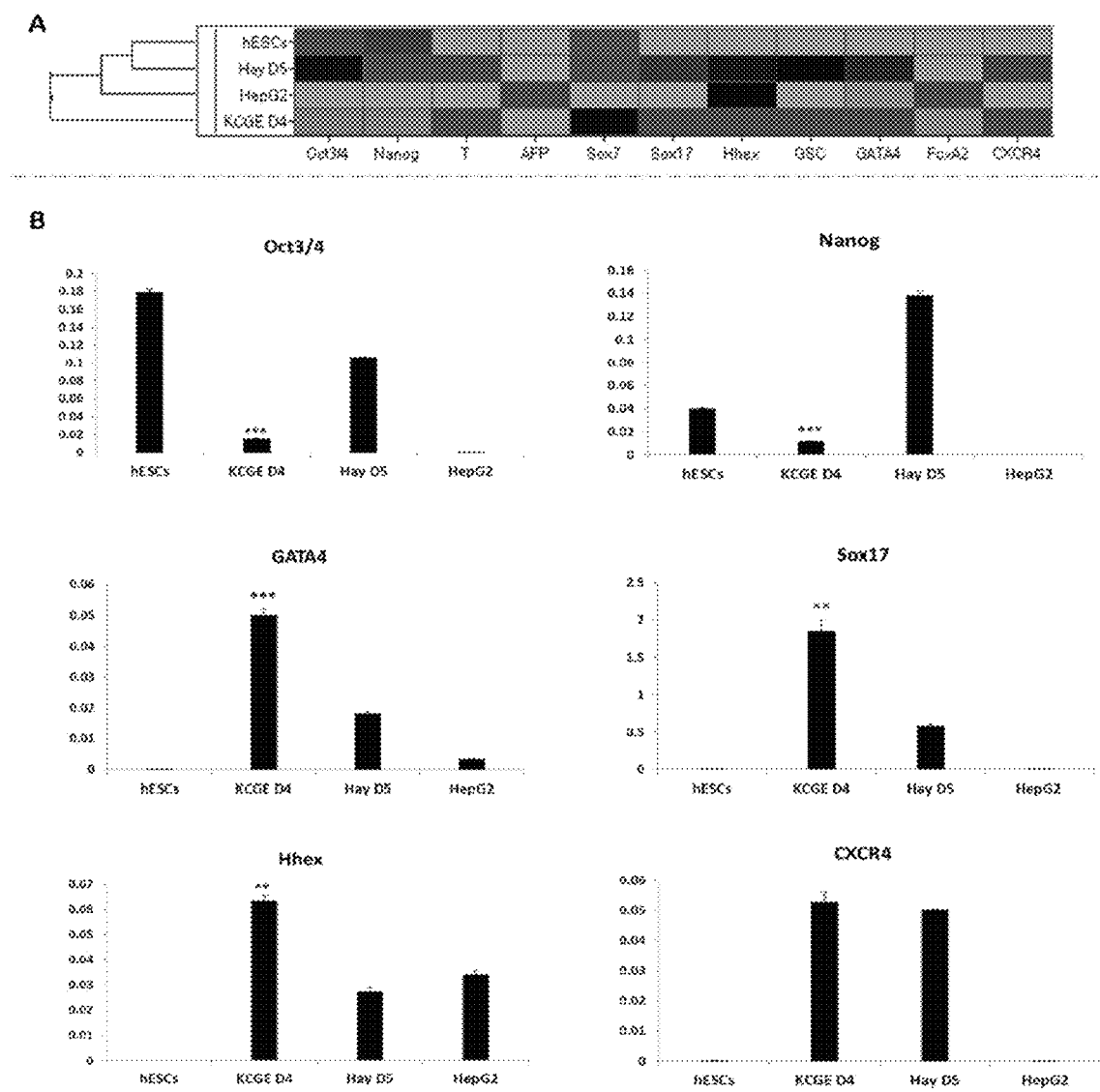
FIG. 6 shows comparison of present invention with prior art method by qRT-PCR analysis.

Comparison of the method of the present invention with an established prior art method (FIG. 6) showed a significant improvement from use of DMSO to potentate the activity of Activin A in DE differentiation. qRT-PCR gene expression profiling (FIG. 6A) of gene pluripotency and differentiation genes in hESC and HepG2 control cells and in hESC differentiated to DE at day 5 using the method of Hay et al (Hay D5) and at day 4 using the DMSO method of the present invention (KCGE D4). (B) qRT-PCR data for individual genes in hESC and HepG2 control cells and in hESC differentiated to DE at day 5 using the method of Hay et al (Hay D5) and at day 4 using the DMSO method of the present invention (KCGE D4). These data show a statistically significant ($p<0.05$ and *$p<0.01$) difference between the standard prior art Hay et al. protocol and the KCGE method of the present invention.

Figure 7:
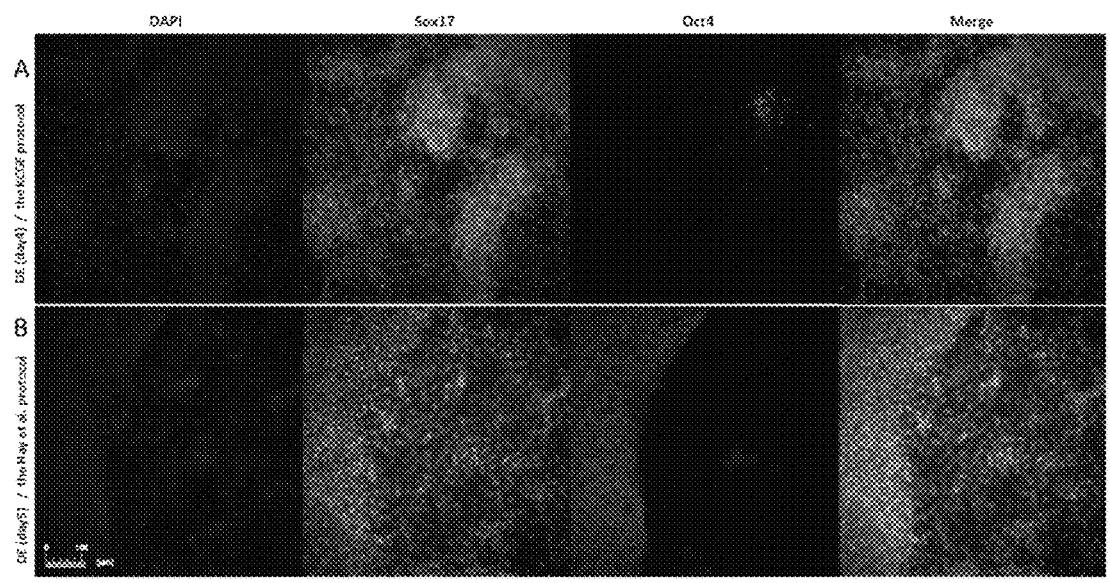
FIG. 7 shows comparison of present invention with prior art method by immunofluorescence.

The improvement provided by the method of the present invention was confirmed by immunofluorescence analysis (FIG. 7) of SOX17 and OCT4 expression in DE cells produced by the prior art Hay et al. method and the KCGE method of the present invention. The method of the present invention produced a large decrease in OCT4 expression and increased SOX17 expression when compared to the prior art method.

Overall these data confirm that DMSO potentiates the action of Activin A in promoting hESC differentiation to DE and subsequently to further differentiated progeny. DMSO has been shown to be active over the concentration range 0.25% to 2% with the most beneficial effects based on gene expression and cell morphology and viability observed in the concentration range 0.25% to 0.75% DMSO, with maximal benefit observed at 0.5%-0.6% DMSO.

While the mechanism of action of DMSO in cell culture and differentiation remains unknown, it is postulated that this small molecule may function partially as histone deacetylase inhibitor (Marks, P. A. and R. Breslow. Nat Biotechnol, 2007. 25(1), 84-90) constraining the activity of histone deacetylase and in turn maintaining chromatin in a less compacted state and thus more available for transcription (Johnstone, R. W., Nat Rev Drug Discov, 2002. 1(4), 287-99). Without being limited to any specific hypothesis, it may be that in definitive endoderm differentiation the addition of DMSO within a specific concentration range to Activin A-based medium increases the availability for expression in DE-priming genes thereby positively affecting the transcription machinery orchestrating formation of this germ layer.

In the present invention, the addition of 0.5% to 0.6% of the small molecule DMSO to the Activin A-based medium during definitive endoderm derivation resulted in a rapid down regulation of pluripotency genes and as a consequence of this effect DMSO significantly potentiated the ability of Activin A to orchestrate definitive endoderm formation. Parallel differentiation of this protocol with the Hay et al protocol which uses the histone deacetylase inhibitor Na Butyrate during DE specification (Hay, D. C., et al., 2008. 26(4), 894-902) further confirmed the significant effects achieved by DMSO in effectively down regulating the pluripotency transcription factor OCT4.

A further and surprising feature of including this small molecule during the DE differentiation stage was observed in the downstream stages of hepatic specification, as shown by the significantly up regulated levels of albumin, demonstrating that short term down regulation of pluripotency genes immediately after initiating cellular differentiation is crucial for cells to efficiently respond long term to the differentiating signals throughout a multi-stage differentiation process.

While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for producing definitive endoderm (DE) cells from primate pluripotent stem cells (pPSC) comprising culturing the pPSC in a medium comprising Activin A and a dimethyl sulfoxide (DMSO), thereby producing DE cells that express a gene selected from the group consisting of SOX17, CXCR4 and GATA4.

2. The method of claim 1, wherein said Activin A is present in said medium at a concentration in a range from 50 ng/ml to 150 ng/ml.

3. The method of claim 2, wherein the Activin A is present in the medium at a concentration of 100 ng/ml.

4. The method of claim 1, wherein said pPSC are cultured in the presence of varying concentrations of said DMSO.

5. The method of claim 4, wherein said DMSO is present in the medium at a concentration in a range from 0.25% to 2% volume/volume.

6. The method of claim 5, wherein the DMSO is present in the medium at a concentration in the range from 0.25% to 0.75% volume/volume.

7. The method of claim 6, wherein the DMSO is present in the medium at a concentration in the range from 0.5% to 0.6% volume/volume.

8. The method of claim 4, wherein the pPSC are initially cultured in the presence of a high concentration of DMSO and then cultured in the presence of a low concentration of DMSO.

9. The method of claim 1, wherein the medium additionally comprises one or more growth factors or modulators selected from the group consisting of FGF2, Wnt3a, SFRP5 and LY294002.

10. The method of claim 1, wherein the pPSC are cultured in the medium for 3 to 5 days.

11. The method of claim 10, wherein the pPSC are cultured in the medium for 4 days.

12. The method of claim 1, wherein the pPSC are selected from the group consisting of human embryonic stem cells or human induced pluripotent stem cells.

* * * * *